United States Patent [19]

Feld et al.

[11] Patent Number: 4,490,297
[45] Date of Patent: Dec. 25, 1984

[54] METHOD FOR THE RECOVERY AND REUSE OF COBALT AND/OR MANGANESE COMPONENTS OF CATALYSTS

[75] Inventors: Marcel Feld, Cologne; Günter Zoche, Bonn-Beuel, both of Fed. Rep. of Germany

[73] Assignee: Dynamit Nobel AG, Troisdorf, Fed. Rep. of Germany

[21] Appl. No.: 451,908

[22] Filed: Dec. 21, 1982

[30] Foreign Application Priority Data

Dec. 24, 1981 [DE] Fed. Rep. of Germany ....... 3151383

[51] Int. Cl.$^3$ .......................... C07F 13/00; C07F 5/06
[52] U.S. Cl. .......................... 260/429 R; 260/439 R; 562/412; 562/414; 562/493; 562/597; 502/24
[58] Field of Search ....................... 560/412, 414, 493; 260/429 R, 439 R; 252/413

[56] References Cited

U.S. PATENT DOCUMENTS

| | | | |
|---|---|---|---|
| 3,332,971 | 7/1967 | Elder et al. | 260/439 R |
| 3,803,191 | 4/1974 | Ehrreich et al. | 260/439 R |
| 3,840,469 | 10/1974 | Hobbs et al. | 260/439 R X |
| 4,170,602 | 10/1979 | Deffeyes et al. | 260/439 R |
| 4,314,073 | 2/1982 | Crooks | 562/412 X |
| 4,329,493 | 5/1982 | Hashizume et al. | 562/414 |
| 4,346,230 | 8/1982 | Hoffmann et al. | 562/412 |

Primary Examiner—Helen M. S. Sneed
Attorney, Agent, or Firm—Felfe & Lynch

[57] ABSTRACT

A process is provided for the recovery and recycling of spent cobalt and/or manganese catalysts used in the air oxidation of alkyl aromatics in acetic acid. The catalysts are isolated in the form of oxalates of extremely low solubility from the acetic acid mother liquors and the cobalt oxalate dihydrate and/or manganese oxalate dihydrate catalysts are restored by the joint action of hydrogen bromide and acetic anhydride, acetyl bromide, or a mixture thereof, to a form in which they are soluble in acetic acid and can be used, again, as oxidation catalysts.

14 Claims, No Drawings

METHOD FOR THE RECOVERY AND REUSE OF COBALT AND/OR MANGANESE COMPONENTS OF CATALYSTS

BACKGROUND OF THE INVENTION

The invention relates to a process for the recovery and reuse of cobalt and or manganese components of catalysts used in the oxidation of alkyl aromatics in acetic acid solution with atmospheric oxygen, such recovery being performed after the separation of insoluble target products or prior to the separation of soluble target products, by the precipitation and separation of the cobalt and/or manganese present in the form of soluble compounds in the mother liquor reaction mixture, by converting them to insoluble cobalt and/or manganese oxalate dihydrate, so that they will be usable in a process for the preparation of terephthalic acid by means of xylene oxidation in acetic acid solution catalyzed either by cobalt and/or manganese bromide, or by other cobalt and/or manganese salts in the simultaneous presence of bromides, as is described, for example, in DE AS No. 1,081,445.

By such methods, however, still other aromatic mononuclear or polynuclear mono-, di- or polycarboxylic acids can be prepared, the aromatics also being additionally to bear one or more identical or different oxidation-resistant groups as substituents. Examples that can be mentioned here are the oxidations of chloro, nitro or tert. butyl toluene to the correspondingly substituted benzoic acids, or dimethylnaphthaline to naphthalinedicarboxylic acid, or of ditolylsulfone to sulfonyldibenzoic acid. In some of these processes, in addition to cobalt or manganese salts and bromides, still other salts are added as cocatalysts or organic promotors.

The recovery and reuse of cobalt and/or manganese salts from the above-named oxidation processes constitute an important problem, but at the same time a difficult one. In a number of processes for the recovery of cobalt and/or manganese catalysts, these heavy metal components are isolated as carbonates from the mother liquor after separation of the target product, in accordance, for example, with DE OS No. 2,131,470, DE OS No. 2,260,491 and DE OS No. 2,419,323. For this purpose the mother liquor must first be concentrated and the concentrate then extracted with water. This process is technically very complex and not without problems. The extraction of the often tarry concentrate, consisting sometimes of two phases, can present considerable difficulty. Together with the cobalt and/or manganese salts, other heavy metals contained as impurities in the mother liquor and hence also in the concentrate may also become precipitated, and then will interfere with the subsequent oxidation when the catalyst is reused.

In JA OS No. 97,593/76 there is described a process for the recovery of cobalt and/or manganese salts from oxidation processes, in which, after the target product has been separated, the cobalt and/or manganese are precipitated from the acetic acid mother liquor by the addition of oxalic acid thereby converting them to oxalates of low solubility, and other heavy metal oxalates can be removed by washing the precipitate. However, the recycling of the virtually insoluble cobalt and/or manganese oxalates to the oxidation process is problematical.

It is the object of the invention to recycle into the oxidation process the cobalt and/or manganese catalysts which have been isolated in the form of very poorly soluble oxalates from acetic acid mother liquors originating in such oxidation processes. No drying process is to be used. This is to be accomplished by restoring the solubility of these catalysts in acetic acid after replacing any catalyst losses that might have been incurred, without thereby impairing the action of the recycled catalyst or adversely affecting the oxidation process by causing secondary reactions, or impairing the yield and purity of the target products. The isolation and recycling of the catalysts is to be repeatable any desired number of times. In other words, the heavy metal catalyst should be able to be precipitated again from the mother liquor that originates from an oxidation process performed with recycled catalyst, and again isolated, and again returned to another cycle of the process.

SUMMARY OF THE INVENTION

In accordance with the invention this object is achieved by subjecting the cobalt and/or manganese oxalate dihydrate, at temperatures of 40° C. to 160° C., preferably 80° C. to 120° C., to the joint action of 2 to 4, preferably 2 to 2.2, moles of hydrogen bromide and 3 to 4, preferably 3.1 to 3.5, moles of acetic anhydride per mole of the cobalt and/or manganese oxalate dihydrate, plus a number of moles of acetic anhydride equal to the number of poles of the water additionally present, thereby converting the cobalt and/or manganese oxalate dihydrate to a form which is soluble in acetic acid and can be used as an oxidation catalyst. The basis of the invention is the observation that the cobalt oxalate, which is virtually insoluble in acetic acid, dissolves therein upon the addition of acetyl bromide (Example 1). A closer study of this surprising finding showed that the same effect can also be achieved by the joint action of acetic anhydride and hydrogen bromide on the oxalate suspended in acetic acid. In other words, the cobalt oxalate, which is only sparingly soluble in hydrobromic acid, but virtually insoluble in water, acetic acid and acetic anhydride, goes into solution in acetic acid under the joint action of acetic anhydride and hydrogen bromide at elevated temperature.

An experiment (Example 3) thus showed that, by suspending 1 part by weight of cobalt oxalate in a solution prepared from two parts by weight of aqueous hydrobromic acid and 8 parts of acetic anhydride, and heating the mixture to a temperature of approximately 80° C., an entirely clear, dark blue solution forms after only 15 minutes, from which no more cobalt oxalate precipitates after any desired amount of dilution with water.

Manganese (II) oxalate, which is also poorly soluble in acetic acid, behaves much like cobalt oxalate, and likewise dissolves therein under the joint action of hydrogen bromide and acetic anhydride.

By taking advantage of the unexpected observation described above, the process of the invention offers an especially simple way of dissolving a still-moist cobalt and/or manganese oxalate isolated from an aqueous or acetic acid solution in a bromide-containing acetic acid, and of using this solution, after adjusting the desired ratios of concentration, as a reaction medium for the oxidation of a suitable aromatic with atmospheric oxygen for the purpose of preparing an aromatic carboxylic acid. After the oxidation, the heavy metal catalyst can then again be precipitated as oxalate, isolated, and again recycled to the oxidation process in accordance with the method of the invention.

The preparation of the acetic acid catalyst solution in accordance with the invention by the joint action of hydrogen bromide and acetic anhydride on cobalt and-/or manganese oxalate can be performed such (Example 3) that all components are combined and the suspension obtained is heated, with stirring. The sequence in which the necessary components are made to act on one another is nevertheless not of basic importance to the process of the invention.

For example, the preparation of the catalyst solution can also be performed by adding acetic anhydride to a suspension of the oxalate in a solution of hydrogen bromide in acetic acid, or by adding hydrogen bromide to a suspension of the oxalate in acetic anhydride or in a mixture of acetic anhydride and acetic acid. In this method of procedure, therefore, acetic anhydride can also be used directly as solvent. If in this case hydrogen bromide is used in the form of an aqueous hydrobromic acid, the hydrolysis of the acetic anhydride provides the temperature of more than 40° C. required for the process of the invention, or the temperature of 80° to 100° C. which is preferred for the rapid and complete dissolution of the oxalate. The addition of acetic anhydride and hydrogen bromide to the suspension of the oxalate in acetic acid can also, however, be performed simultaneously or alternately.

If one is willing to get together the necessary amount of acetic anhydride, say for the purpose of making up for solvent losses in the oxidation process, the acetic anhydride can also be fed to a suspension of the cobalt and/or manganese oxalate in aqueous hydrobromic acid, the water being used up by the hydrolysis of acetic anhydride, and thus a suspension of the oxalate in acetic acid will result. Basically, the solid might also be added portion-wise to the heated solution of the rest of the components, but such a procedure is not recommendable, for technical reasons. Lastly, the possibility ought not to be excluded of using some or all of the alkyl aromatics that are to be oxidized, in preparing the catalyst solution in accordance with the invention.

The hydrogen bromide can be put in either in gaseous form or in the form of an aqueous or acetic acid solution, or in the form of a solution of hydrogen bromide in acetic anhydride. It is furthermore possible to use, instead of hydrogen bromide, a compound such as, for example, acetyl bromide, which is capable of forming the hydrogen bromide by reaction with acetic acid or water. Acetyl bromide in the appropriate amount is not only a substitute for the hydrogen bromide, but at the same time it replaces the acetic anhydride (Example 1). For reasons of cost, the use of acetic anhydride and hydrogen bromide, however, appears to be especially desirable and is therefore preferred.

The amount of acetic anhydride that is needed when hydrogen bromide is used depends not only on the amount of the cobalt and/or manganese oxalate that is to be dissolved, but also on the water content of the acetic acid, the oxalate and the hydrobromic acid. In the case of the use of anhydrous acetic acid, anhydrous hydrogen bromide, and in the case of the use of cobalt and/or manganese oxalate in the form of the dihydrates without any additional residual content of water, three (3) moles of acetic anhydride are required per mole of the heavy metal oxalate that is to be dissolved. An excess of acetic anhydride, however, does not have any adverse effect on the process and is quite desirable for the acceleration and completeness of the dissolving process.

If one or more of the components used in the process of the invention for the preparation of an acetic acid solution of the insoluble cobalt and/or manganese oxalate contain water, a molar excess of acetic anhydride in relation to the water content is necessary. This applies also, for example, to the use of an aqueous hydrobromic acid, or when the oxalate is washed with water to eliminate other heavy metals and is then subjected to the process herein described while still moist.

On the other hand, the amount of acetic anhydride can be reduced if acetyl bromide is used instead of hydrogen bromide. In this case even one mole of acetic anhydride plus two moles of acetyl bromide per mole of the oxalate will suffice, slight excesses of both components being again desirable.

The amount of hydrogen bromide which is required together with acetic anhydride for the preparation, in accordance with the invention, of the acetic acid catalyst solution of cobalt and/or manganese oxalate depends exclusively on the concentration of the heavy metals in the solid. For the complete dissolution of the oxalates, at least the stoichiometric amount is necessary, i.e., two moles of hydrogen bromide per mole of cobalt or manganese oxalate. If these stoichiometric amounts of hydrogen bromide are used, care must of course be taken to see that no hydrogen bromide losses are incurred by escaping at the elevated temperature of preferably 80° to 100° C., i.e., the operation must be performed in a closed, pressure-resistant apparatus, or else the loss of hydrogen bromide must be compensated. Since on the other hand an excess of hydrogen bromide entails no fundamental disadvantage for the process of the invention, such an excess of, say, 5 to 10% by weight more than the stoichiometric amount is quite desirable for the rapid and complete dissolving of the heavy metal oxalate.

The amount of hydrogen bromide needed for the dissolution of the cobalt and/or manganese oxalate does not necessarily determine the ratio of heavy metal ions to bromide in the reaction medium. If in the oxidation a great excess of bromide with respect to cobalt and/or manganese is desired, it can be established by using an appropriately large amount of hydrogen bromide in the preparation of the catalyst solution. The process, however, also offers the possibility of a subsequent reduction of the bromide concentration if it appears desirable or necessary for certain oxidation processes in order to achieve optimum catalyst ratios or to reduce the corrosive action of such a solution.

A subsequent reduction of the bromide concentration in the acetic acid solution of cobalt and/or manganese oxalate prepared with the joint action of hydrogen bromide and acetic anhydride is accomplished by the addition of appropriate basic salts, oxides or hydroxides. In this case those combinations of such cations are to be considered as suitable which on the one hand will form a bromide that is very poorly soluble in acetic acid, and which on the other hand will not have any adverse effect on the subsequent oxidation, in relatively low concentration.

Substances suitable for the reduction of the bromide ion concentration in the catalyst solution prepared in accordance with the invention are acetates, carbonates, hydroxides and oxides from the series of the alkali metals and of ammonium. In order in this step of the process to prevent precipitation of anhydrous cobalt or manganese acetate, provision must be made for a sufficient, i.e., relatively great, dilution of the acetic acid, or else for a sufficient water content in the solution. A sufficient water content is present when the solution, at a cobalt or manganese concentration of approximately 3 to 1 percent by weight which is typical for the process of the invention, for each part of cobalt and/or manganese by weight, contains about 1 to 2 parts by weight of water. This amount of water can be added to the catalyst solution together with the basic substance, but it can also be added previously or subsequently thereto.

The reduction of the bromide content in the catalyst solution prepared from cobalt and/or manganese oxalate is then performed by adding the basic substance and the water, and then isolating the crystalline bromide formed from the cation of the basic substance and the bromide in the catalyst solution by a conventional method of separating solids from liquids. In this case it may be necessary or desirable to heat the suspension sufficiently prior to the separation of the bromide.

The amount of the basic substance which it is necessary to add depends upon the solubility of the bromide in acetic acid and on the initial bromide content and the final bromide concentration desired in the solution. If the solution prepared from 1 weight-part of cobalt oxalate dihydrate, 2 weight-parts of a 48 wt.-% hydrobromic acid and 8 weight-parts of acetic anhydride (Example 3) is treated with 0.9 weight-parts of 30 wt.-% aqueous ammonia solution, then 0.9 weight-parts of ammonium bromide can be isolated. The solution then still has a cobalt-to-bromide weight ratio of 3:1. If the above solution (Example 3) is treated with 0.5 weight-part of water and one weight-part of potassium acetate, then 0.9 weight-parts of potassium bromide can be isolated, and then a cobalt-to-bromide weight ratio of 1.7:1 can be detected in the solution. Any desired higher ratio of cobalt to bromide can be established by greater dilution and by adding less alkali.

The solution prepared by the method of the invention from cobalt and/or manganese oxalate by the action of acetic anhydride and hydrogen bromide and corrected, if desired, as regards the bromide content, can be used as catalyst solution for the oxidation reactions in acetic acid solution catalyzed by cobalt and/or manganese salts in combination with bromides. The progress and result of an oxidation of p-xylene to terephthalic acid in acetic acid, catalyzed by means of a fresh catalyst solution prepared from cobalt acetate and potassium bromide corresponded entirely to the progress and the result of oxidation using a catalyst solution prepared in accordance with the invention under otherwise the same experimental conditions.

Thus, the oxidation of 1 weight-part of p-xylene in 5 weight-parts of acetic acid, catalyzed by 0.05 weight-parts of cobalt acetate tetrahydrate and 0.014 weight-parts of potassium bromide, at 180° C., 25 bar, and an average air input of 1.8 liters per minute, per mole of xylene in the starting mixture resulted in a yield of terephthalic acid of 94 mol%. 3.2 moles of oxygen were absorbed per mole of p-xylene over a period of 252 minutes (Example 9). Almost identical results were obtained with regard to terephthalic acid yield (93.9 mol-%), reaction time (254 min) and oxygen absorption (3.2 moles per mole of p-xylene), in the experiment performed under comparable reaction conditions, with a catalyst solution of equal cobalt and bromide concentration prepared by the method of the invention from cobalt oxalate.

After removing the target product from the mother liquors of these experiments, it was then possible to separate and isolate the cobalt from them, and then to use them for preparing a reusable catalyst solution.

The method of the invention will be further explained with the aid of the following examples.

EXAMPLES

Example 1

A suspension of 14.7 g of cobalt oxalate dihydrate in 100 g of acetic acid was treated by adding 33 g of acetyl bromide drop by drop, with stirring, and maintaining it for one hour at the reflux temperature. The solid dissolved completely, forming a dark blue solution. No precipitation followed the addition of first 10, then 50 ml, of water.

Example 2

A suspension of 14.7 g of cobalt oxalate dihydrate in a mixture of 100 g of acetic acid and 9 g of acetic anhydride was treated by adding acetyl bromide drop by drop, with stirring, at the refluxing temperature. After the addition of 22 g of acetyl bromide, a completely clear, dark blue solution had formed, from which no cobalt oxalate precipitated upon the addition of water.

Example 3

In a solution prepared from 29.4 g of 48 weight-percent hydrobromic acid and 118 g of acetic anhydride, 14.7 g of cobalt oxalate dihydrate was suspended. Upon heating this suspension with stirring, the solid went increasingly into solution. After about 15 minutes at 75° to 85° C., a completely clear, dark blue solution had formed.

Example 4

9.8 g of manganese acetate tetrahydrate was dissolved in 18 g of water and then the dissolved manganese was precipitated as oxalate by the addition of 5 g of oxalic acid dihydrate. Then 200 g of acetic anhydride was added, 22.4 g of a 40 weight-percent hydrobromic acid was stirred into the suspension thus formed, and the mixture was heated. After about 10 minutes under refluxing conditions a completely clear solution had formed, from which no manganese oxalate precipitated after dilution with any desired amount of water.

Example 5

The dark blue solution prepared in accordance with Example 3 was treated with 14.9 g of a 30 weight-percent aqueous ammonia solution, then refluxed for 2 hours with stirring, cooled to room temperature, and filtered. The filter cake was washed twice with 30 g of acetic acid, and the white salt obtained was dried. The product was 14.8 g of $NH_4Br$. The mother liquor was combined with the washing filtrate and acetic acid was added to make 245 g, and the bromide concentration therein was found to be 0.6% by weight.

Example 6

The solution prepared in accordance with Example 3 was treated with 7.8 g of water and 15.9 g of potassium acetate; it was then refluxed with stirring for 2 hours, and processed as in Example 5. The product was 14.9 g of KBr. The bromide content of the mother liquor, after being combined with the washing filtrate and with enough acetic acid to make 335 g, amounted to 0.75 wt.-%.

Example 7

The solution prepared in accordance with Example 3 was treated with 19.9 of a 50 weightpercent aqueous potassium hydroxide solution and refluxed with stirring for 2 hours. Then it was processed as described in Example 5. The product was 15 g of KBr and 192 g of mother liquor with a bromide concentration of 1.93 wt.-%.

Example 8

96 g of the mother liquor obtained in Example 7 after separation of the potassium bromide (corresponding to an input of 2.37 g of cobalt and 1.85 g of bromide) was heated at 180° C. at 25 bar with 200 g of p-xylene and 917 g of acetic acid. Then air was passed through the solution, with stirring, at a constant output rate of 3 liters per minute. The progress of the reaction was followed by constantly checking the oxygen content in the exhaust gas. The oxygen absorption stopped after a reaction time of 254 minutes. 294.0 of terephthalic acid was separated by means of a pressure filter from the reaction mixture after cooling the latter to room temperature. Over the period of 254 minutes of reaction time, 147.8 liters of oxygen had been absorbed. After the addition of 4.7 g of oxalic acid to the mother liquor combined with the washing filtrates, 7.3 g of cobalt oxalate dihydrate was isolated.

Example 9 (Example for purposes of comparison)

The experiment described in Example 8 was performed with the use of 200 g of p-xylene, 1000 g of acetic acid, 10 g of cobalt acetate tetrahydrate (corresponding to 2.37 g of cobalt) and 2.75 g of potassium bromide (corresponding to 1.86 g of bromine). After a reaction time of 252 minutes and an oxygen absorption of 147.2 liters, 294.5 g of terephthalic acid was obtained. After the addition of 4.7 g of oxalic acid, 7.4 g of cobalt oxalate dihydrate was isolated from the mother liquor.

It will be understood that the specification and examples are illustrative but not limitative of the present invention and that other embodiments within the spirit and scope of the invention will suggest themselves to those skilled in the art.

What is claimed is:

1. A process for the recovery of spent cobalt and/or manganese catalyst used for the air oxidation of alkyl aromatics in acetic acid solution wherein cobalt and/or manganese catalyst metals are precipitated from the acetic acid as acetic acid insoluble cobalt and/or manganese oxalate dihydrate salts; comprising the conversion of the insoluble oxalate dihydrate salts into an acetic acid soluble form by reaction with acetyl bromide, hydrogen bromide or a mixture thereof in acetic acid or acetic anhydride.

2. The process of claim 1 wherein 2 to 4 moles of hydrogen bromide and 3 to 4 moles of acetic anhydride per mole of cobalt and/or manganese oxalate dihydrate, are used.

3. The process of claim 1 wherein the converting reaction temperature is maintained from about 40° C. to about 160° C.

4. The process of claim 3 wherein the reaction temperature is from about 80° to 120° C.

5. The process of claim 1 wherein 2 to 2.5 moles hydrogen bromide and 3.1 to 3.5 moles of acetic anhydride per mole of the cobalt and/or manganese oxalate dihydrate are used.

6. The process of claim 5 wherein the reaction temperature is about 80° C. to 120° C.

7. The process of claim 1 wherein the insoluble cobalt and/or manganese oxalate dihydrate is suspended in acetic acid before being converted.

8. The process of claim 1 wherein the conversion reaction mixture comprises acetyl bromide.

9. The process of claim 8 wherein the reaction mixture comprises at least one mole of acetic anhydride and two moles of acetyl bromide, per mole of oxalate.

10. The process of claim 1 further comprising reducing the bromide concentration of the soluble salts by adding a salt, oxide, or hydroxide having a cation which forms an insoluble bromide, to the soluble salt, and removing the resulting precipitate.

11. The process of claim 10 wherein an acetate, carbonate, or hydroxide of sodium, potassium, or ammonium, is used.

12. The process of claim 11 wherein sufficient water is added so that the solution contains 0.5 to 3 parts by weight water per part by weight dissolved cobalt and/or manganese.

13. The process of claim 12 wherein 1 to 2 parts water are used.

14. The process of claim 1 wherein hydrogen bromide is used as aqueous hydrobromic acid or as a solution in acetic acid.

* * * * *

UNITED STATES PATENT AND TRADEMARK OFFICE
CERTIFICATE OF CORRECTION

PATENT NO. : 4,490,297
DATED : December 25, 1984
INVENTOR(S) : Marcel Feld et al.

It is certified that error appears in the above-identified patent and that said Letters Patent is hereby corrected as shown below:

Col. 1, line 26, after "being" insert -- able --.

Col. 2, line 28, "poles" should be -- moles --.

Col. 6, line 68, "filtrate" should be -- filtrates --.

Col. 7, line 37, "1.86" should be -- 1.85 --.

Signed and Sealed this

Twenty-eighth Day of May 1985

[SEAL]

Attest:

DONALD J. QUIGG

Attesting Officer

Acting Commissioner of Patents and Trademarks